United States Patent [19]

Illig et al.

[11] Patent Number: 5,260,049

[45] Date of Patent: Nov. 9, 1993

[54] X-RAY CONTRAST COMPOSITIONS COMPRISING ALKOXYPHENOLS

[75] Inventors: Carl R. Illig, Phoenixville; John L. Toner, Downingtown, both of Pa.

[73] Assignee: Sterling Winthrop Inc., Malvern, Pa.

[21] Appl. No.: 876,933

[22] Filed: May 1, 1992

[51] Int. Cl.$^5$ .................. G01N 203/084; A61K 31/34; A61K 31/075; C07C 41/00
[52] U.S. Cl. ......................................... 424/5; 514/473; 514/717; 514/941; 514/942; 568/580; 568/656
[58] Field of Search ............... 424/5, 4; 514/717, 941, 514/942, 473; 568/580, 656

[56] References Cited

U.S. PATENT DOCUMENTS

| | | | |
|---|---|---|---|
| 2,613,172 | 10/1952 | Galler | 167/95 |
| 2,622,100 | 12/1952 | Newbery et al. | 260/612 |
| 3,795,698 | 3/1974 | Soulal et al. | 260/471 R |
| 5,106,407 | 4/1992 | Relenyi et al. | 424/5 |

FOREIGN PATENT DOCUMENTS 1259565 12/1989 Canada .
1481943 5/1967 France .

OTHER PUBLICATIONS

Hebky, J. et al. Collect. Czech. Chem. Commun. 41(10):3094–3105 (1976).
Acta Pharm. Suecica 11:33–48 (1974) Carnmalm et al.

*Primary Examiner*—Glennon H. Hollrah
*Assistant Examiner*—Gary E. Hollinden
*Attorney, Agent, or Firm*—Arthur Rosenstein; Imre Balogh

[57] ABSTRACT

Disclosed are aqueous compositions containing a contrast agent of the formula

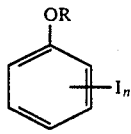

(I)

and methods for their use in diagnostic radiology of the gastrointestinal tract, wherein R is a substituted or unsubstituted alkyl group containing from 2 to 8 carbon atoms, wherein said substituents are selected from the group consisting of $C_1$–$C_6$ alkyl, hydroxy and alkoxy; and n is 1 to 5.

4 Claims, No Drawings

X-RAY CONTRAST COMPOSITIONS COMPRISING ALKOXYPHENOLS

BACKGROUND OF THE INVENTION

1. Field of the Invention

This invention relates to aqueous compositions containing contrast agents and methods for their use in diagnostic radiology of the gastrointestinal tract.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

The most widely used contrast agents for the visualization of the GI tract is barium sulfate administered as a suspension orally or rectally as an enema. (See, for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos. 2,786,055; 3,795,698; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

We had surprisingly found that certain compounds hereinafter described posses these desirable properties when used in aqueous oral and rectal formulations for examination of the GI tract utilizing X-rays and CT scans.

SUMMARY OF THE INVENTION

The present invention provides an aqueous, oral or retrograde composition for radiological examination of the GI tract comprising a contrast agent having the formula (I)

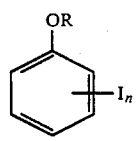

(I)

wherein R is a substituted or unsubstituted alkyl group containing from 2 to 8 carbon atoms, wherein said substituents are selected from the group consisting of $C_1$-$C_6$ alkyl, hydroxy and alkoxy; and n is 1 to 5.

Preferred contrast agents of the present invention have the formula:

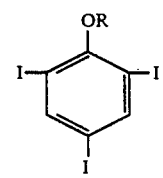

wherein R is a secondary alkyl group containing from 4 to 8 carbon atoms.

The most preferred contrast agent utilized by the present invention is the sec-octyl ether of 2,4,6-triiodophenol having the formula:

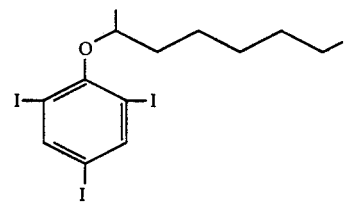

The compounds are readily synthesizable by methods known in the prior art. The compounds' desirable properties include: sufficient iodine content for producing adequate imaging; ability to coat the mucosal lining of the GI tract giving good imaging quality; and superior toxicological profile.

The compositions may be in the form of dispersions, colloids or suspensions, however, we prefer to use emulsions as the preferred embodiments.

DETAILED DESCRIPTION OF THE INVENTION

The contrast agents utilized in the compositions of the present invention are slightly soluble in water, having a partition coefficient equal or greater than 10. This degree of solubility allows the formation of stable formulations in the form of dispersions, emulsions, suspensions when the formulations contain the requisite excipients. The term "stable" means that there is no separation of the ingredients contained in the compositions after oral or rectal administration thereof and during radiological examination of the GI tract. The slight solubility of the contrast agents in aqueous media permits diffusion of the contrast agents into the intestinal mucosa and secretions thereby forming a coating on the intestines. On the other hand, due to their slight solubility, the absorption of the contrast agent into the intestinal walls is minimal which reduces the possibility of toxic side effects.

Some of the contrast agents of the present invention can be prepared as described in U.S. Pat. No. 2,622,100, the disclosure of which is incorporated herein by reference. We, however, prefer utilizing the preparative methods described in the examples that follow.

EXAMPLE 1

A. 2-Mesyloxyoctane

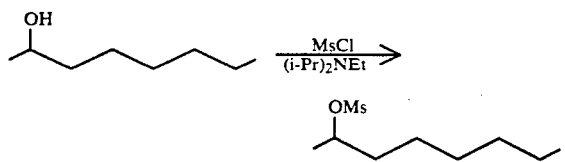

To 130 g (0.995 mol) of 2-octanol and 207 ml (1.19 mol, 1.2 equiv) of diisopropylethylamine in 1.5 L dichloromethane at 0° C. under a $CaSO_4$ drying tube was added dropwise 84.4 ml (1.09 mol, 1.1 equiv.) of methanesulfonyl chloride over 1 hour while keeping the internal temperature at less than 5° C. The faintly yellow solution was stirred at 0° C. for an additional 1.5 h. The cold reaction solution was then washed with 2×1 L ice-cold 1M HCl and 1 L of ice-cold $H_2O$ and brine and dried over $MgSO_4$. The residue was filtered through Celite and concentrated in vacuo below 35° C. to afford 208 g of a yellow oil. The yellow oil was placed under high-vacuum for 2 h at 25° C. to give 205 g of yellow oil. NMR spectra confirmed the desired title-product having only trace amounts of solvents present.

B. 2,4,6-Triiodophenoxy-2-Octane

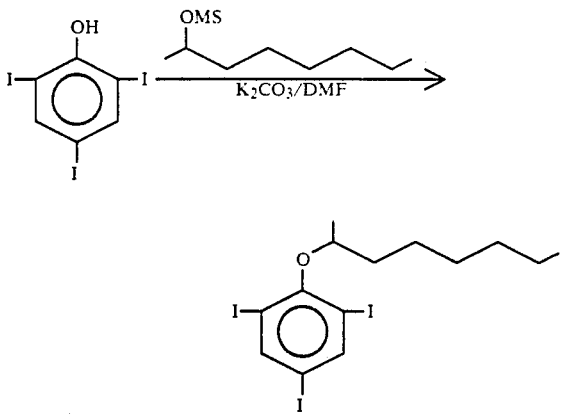

To a 5 L round bottom flask equipped with a mechanical stirrer was added, under nitrogen, 71.3 g (0.342 mol) of 2-mesyloxyoctane (obtained in A), 193 g (0.410 mol, 1.2 equiv) of 2,4,6-triiodophenol, 56.7 g (0.410 mol, 1.2 equiv.) of anhydrous potassium carbonate and 2.00 L of dimethylformamide (hereinafter DMF). The mixture was warmed slowly over one hour to reach a temperature of 55° C. to 60° C. and then stirred at 55° C. for 16 hours.

The temperature was raised to 65° C. and the mixture stirred for an additional 4 hours, then slowly cooled to room temperature and filtered through Celite to remove solids. The amber-colored DMF filtrate was extracted with 3×500 ml hexane to remove some of the product (first extract). TLC (25% EtOAc-hexane) indicated that the extract was the extremely pure title-product.

The DMF solution remaining after extraction with hexane was diluted with 9 L $H_2O$ and 1 L of 1M NaOH. This mixture was extracted with 3×750 ml hexane (second extract). TLC showed that the extract was somewhat less pure than the first extract, but still only contained minor impurities.

The first extract and second extract were then separately washed with 2×500 ml of 1M NaOH, 500 ml of $H_2O$, 500 ml of saturated $Na_2SO_3$, 4×1 L $H_2O$, 1 L of brine and dried over $Na_2SO_4$.

Concentration in vacuo followed by high vacuum afforded from the first extract 65.5 g of a faintly yellow oil (33% yield). NMR spectra confirmed the extremely pure title-product containing no measurable amount of other materials, such as unreacted mesylate.

The second extract afforded 92.2 g (46% yield) of a light amber-colored oil. NMR spectra confirmed a reasonably pure product having only trace amounts of impurities, such as mesylate.

The 65.5 g of product obtained from the first extract was filtered through 500 g of silica eluting with 6 L of hexane to remove the trace of yellow color. Concentration in vacuo and under high vacuum and warming for 15 minutes afforded 64.7 g of the pure, colorless oil (99% recovery). NMR spectra confirmed the same very pure product as before.

The 92.2 g of product obtained from the second extract was subjected to the same procedure as the first extract. The product was found to be pure (98% recovery) without having a yellow color and without trace amounts of impurities, such as mesylate.

EXAMPLE 2

2,4,6-Triiodophenoxy-2-Butane

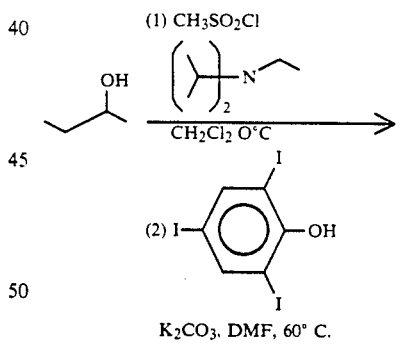

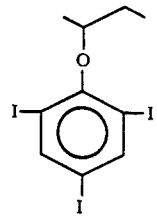

To a solution of 45.0 mmol of 2-butanol (4.1 ml) in dichloromethane at 0° C. was added 1.2 equiv. (9.4 ml) of diisopropylethylamine. After about 10 minutes, 1.1 equiv. (4.8 ml) of methanesulfonyl chloride was added slowly by syringe over about 10 min. The solution was stirred in an ice/water bath for 2.5 h, then poured over cold 5% HCl. The layers were separated and the organic layer was washed with cold 5% aqueous HCl and brine and dried over Na$_2$SO$_4$. The dried residue was dissolved in DMF (100 ml) and 50.0 mmol (23.6 g) of 2,4,6-triiodophenol was added which was followed by the addition of 50.0 mmol (6.9 g) of potassium carbonate. (The solution at this point turned dark and was difficult to stir). Stirring continued for 17 h. The solution was then cooled, filtered through Celite using DMF. The so-obtained DMF-containing solution was twice extracted with hexane, diluted with 200 ml of 0.1M aqueous NaOH and again extracted twice with hexane. The hexane extracts were combined and washed with 2×50 ml 1M NaOH, 2×50 ml H$_2$O and brine. The organic layer was dried over Na$_2$SO$_4$, filtered and the solvent removed in vacuo. Purification of the residue by flash column chromatography (silica, hexanes) gave 9.9 g of the title product as an oil.

An alternate method of making the compound of Example 2 is described in Example 3.

EXAMPLE 3

2,4,6-Triiodophenoxy-2-Butane

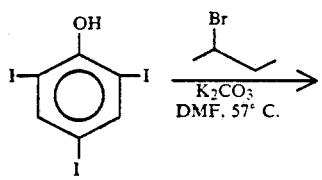

To a solution of 21.19 mmol (10.0 g) of 2,4,6-triiodophenol in 40 ml (0.5M) DMF at room temperature was added 2.0 equiv (4.6 ml) of 2-bromobutane and 2.0 equiv. (5.86 g) of potassium carbonate. The mixture was heated to 57° C. in an oil bath and stirred for 65 h. The mixture was then cooled, filtered through Celite by washing with DMF. The DMF-containing solution was extracted with hexane, diluted with 10% NaOH (100 ml) in H$_2$O, and extracted 3 times with hexane. The extracts were combined and washed twice with 1M NaOH, twice with H$_2$O and twice with brine. The organic layer was dried over Na$_2$SO$_4$, filtered and the solvent was removed in vacuo. Purification by flash column chromatography (hexanes, silica) yielded 10.83 g of the title product in the form of an oil.

EXAMPLE 4

2,4,6-Triiodophenoxy-2-Hexane

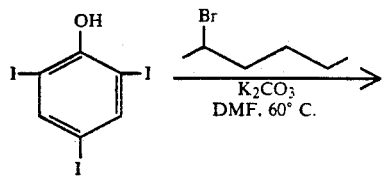

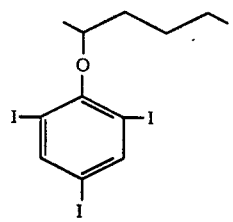

To a solution of 63.6 mmol (30 g) of 2,4,6-triiodophenol in 125 ml of DMF (0.5M) at room temperature was added 1.2 equiv. (10.8 ml) of 2-bromohexane and 1.5 equiv. (13.2 g) of potassium carbonate. The mixture was heated to 58° C. over 1.5 h, then stirred 40 h. The reaction mixture was filtered through Celite using DMF. The volume of DMF was reduced to 200 ml by evaporation in vacuo. The mixture was extracted twice with hexane, diluted with 500 ml of 10% NaOH in H$_2$O and extracted again with hexane 3 times. The hexane extracts were then combined and washed twice with 1M NaOH, twice with H$_2$O and once with brine. The organic layer was then dried over Na$_2$SO$_4$, filtered and the solvent was removed in vacuo. Flash column chromatography (hexanes, silica) yield 31.5 g of the title compound in the form of an oil.

EXAMPLE 5

4-Iodophenoxy-2-Octane

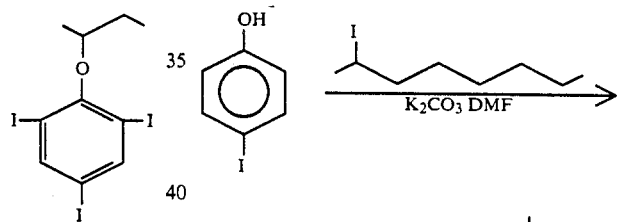

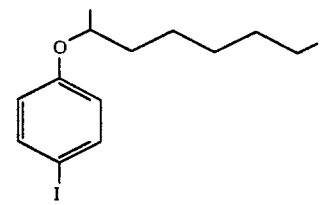

A mixture of 50.0 g (0.227 mol) of 4-iodophenol, 45.4 g (0.189 mol) of 2-iodooctane and 94.1 g (0.681 mol) potassium carbonate in 500 ml dry acetonitrile was heated to reflux under nitrogen and stirred for 20 h. The mixture was cooled and filtered through Celite and concentrated in vacuo. The brown residue was partitioned between 1 L hexanes and 500 ml 1M NaOH. The hexane layer was then washed with 1M NaOH (3×250 ml) saturated sodium sulfite (250 ml), water (250 ml) and brine (250 ml). The faintly yellow solution was dried over Na$_2$SO$_4$ and concentrated in vacuo to 34.3 g of a light yellow oil. The material in 60 ml of hexane was passed through a 600 g pad of silica gel eluting with 3% ethyl acetate-hexanes until just prior to elution of the yellow color. Concentration and warming under high vacuum afforded 26.9 g (43%) of product as a mobile colorless oil.

Other compounds of formula I may be prepared using the reaction techniques described in Examples 1 through 5 using appropriate starting materials and reagents. It is to be understood that all reaction conditions, including choice of solvents, reaction atmosphere, reaction temperature, duration of the experiment and workup procedures, are chosen to be conditions standard for that reaction, which should be readily recognized by one skilled in the art. It is understood by one skilled in the art of organic synthesis that the functionality present on portions of the educt molecule must be compatible with the reagents and reactions.

Starting materials, reagents and solvents can be obtained from chemical suppliers, such as Aldrich, Baker and Eastman Chemical Companies, or they may be prepared by techniques known in the prior art.

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

COMPOSITIONS

Compositions of the present invention comprise the following pharmaceutically acceptable components based on % w/v:

| | |
|---|---|
| Non-aqueous phase | 1-50 |
| Contrast Agent | 0.001-75 |
| Excipient | 0-20 |
| Aids/Surfactants/Emulsifiers) | 0.01-10 |
| Water | q.s. to 100 |

The nonaqueous phase comprises vegetable oils such as safflower oil; non-metabolizing fat substituents, such as Simpless; fluorinated hydrocarbons, such as perfluorodecaline; mineral oil and simethicone.

The contrast agents are selected from the group of compounds of formula I, preferably compounds wherein R is an alkyl group containing from 4 to 8 carbon atoms.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 5% w/v of the aqueous formulations, although the amount, in general, is kept as low as possible, preferably in the range of 0.05 to 2% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyhydric alcohols, for example glycerol, glycols such as mono-, di-, tetra-and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamines and diethylamides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

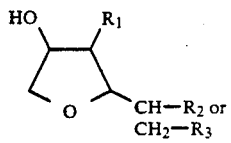

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=(C_{11}H_{23})COO$ for laurate, $(C_{17}H_{33})COO$ for oleate, $(C_{15}H_{31})COO$ for palmitate, $(C_{17}H_{35})COO$ for stearate.

Polyoxyethylene alkyl ethers (i.e. Brijs) having the formula:

$$CH_3(CH_2)_x(O-CH_2-CH_2)_yOH$$

where $(x+1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10-60.

Polyethylene sorbitan fatty acid esters, sold under the trade names of Polysorbates 20, 40, 60, 65, 80 and 85.

Polyethylene stearates, such as:
poly(oxy-1,2-ethanediyl),α-hydro-ω-hydroxy-octadecanoate;
polyethylene glycol monostearate; and
poly(oxy-1,2-ethanediyl)-a-(1-oxooctadecyl)-w-hydroxy-polyethylene glycol monostearate Exemplary formulations of the present invention are as shown:

| Example 6 | |
|---|---|
| Compound of Example 1 (114 mg I/ml) | 2.50 g (17.5% w/v) |
| Dow Corning Med. Antifoam AF emulsion | 3.50 g (35% w/v) |
| Purified Water | q.s. to 10 ml |
| Example 7 | |
| Compound of Example 1 (114 mg I/ml) | 2.50 g (17.5% w/v) |
| Safflower Oil | 2.00 g (20% w/v) |
| Tween-21 | 0.25 g (2.5% w/v) |
| Hydroxypropyl methylcellulose (4,000 cPs) | 2.50 g of 2% solution |
| Purified Water | q.s. to 10 ml |
| Example 8 | |
| Compound of Example 1 (114 mg I/ml) | 2.50 g (17.5% w/v) |
| Mineral Oil | 0.50 g (5% w/v) |
| Tween-21 | 0.25 g (2.5% w/v) |
| Purified Water | q.s. to 10 ml |
| Example 9 | |
| Compound of Example 1 (114 mg I/ml) | 2.50 g (17.5% w/v) |
| Simplesse 100 (Nutrasweet Co.) | 3.00 g (30% w/v) |
| Hydroxypropyl methylcellulose (4000 cPs) | 2.50 g of 2% solution |
| Purified Water | q.s. to 10 ml |

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% v/v and most preferably of from about 0.1% w/v to about 20% w/v.

Compositions of the present invention were tested for toxicity and X-ray imaging qualities as herein described.

TOXICOLOGICAL TESTING

The sec-octyl ether of 2,4,6-tri-iodophenol, prepared in Example 1, was emulsified as follows: 25% w/v of the compound (containing 163 mg I/ml) was emulsified in 35% w/v Dow Corning Medical Antifoam AF emulsion and 40% w/v water. The 35% w/v Dow Corning Medical Antifoam AF emulsion in water served as both the control and vehicle for the test compound.

Male Swiss-Webster albino mice (obtained from Teconic Farms, Germantown, NY) were used for the experiment. Treatment groups consisted of three mice each, 32 days old, which were fasted for 4 hours prior to dosing. Food was provided ad libitum, after dosing. The emulsified compound was administered once orally by gavage at dosages of 1633, 3266 and 6532 mg I/kg in volumes of 10, 20 and 40 ml/kg respectively. An additional group of three mice were similarly administered 40 ml/kg of the 35% Dow Corning emulsion which served as controls. All animals were dosed on the same day and were observed for changes in appearance and behavior and for mortality at multiple intervals on the day of dosing and at least once daily thereafter for 14 days. In addition to Day 1 weights (prior to dosing), the mice were weighed on Days 2, 8 and 15. At the end of the study (Day 15), the mice were killed with intraperitoneal injection of sodium pentabarbital and necropsied.

There were no clinical signs observed for mice given the control emulsion or those given the test compound-containing emulsion. Body weight changes were comparable among the groups. At necropsy, special attention was given to the gastrointestinal tract, but no abnormalities were detected.

X-RAY IMAGING—UPPER GI TRACT

In another experiment, the above formulation was used for GI imaging of the upper GI tract of dogs using X-rays. Each of the doges in the experiment received 300 ml of the formulation by NG tube. A uniform air contrast coating of the small bowel occurred. Transradiation was also present. The underlying bowel loops were also visible.

X-RAY IMAGING—LOWER GI TRACT

X-ray images, were also taken after 4 hours after 24 h of administration, i.e. images were taken from the lower GI tract of the same dogs.

The uniform mucosal coating was found to be somewhat less effective than at the time of initial imaging (upper GI tract). However, the uniformity of radiopacity and mucosal coating on delayed images were still close to optimal.

X-RAY IMAGING—COLON

The emulsion formulation containing the above contrast agent was also tested in the form of an enema administered to dogs for X-ray visualization of the lower GI tract. Each of two dogs received 500 ml of the formulation, followed by drainage of the material and installation of air. Radiographs were taken before air administration (single contrast) and after air administration (double contrast) to permit comparison of the results.

The single contrast images demonstrated adequate radiodensity of the full column of contrast, while preserving visibility of the underlying structure, similar to that seen in the upper GI studies.

Double contrast imaging showed excellent mucosal coating throughout the colon. The mucosal coating and colon visualization was preserved even after 30 minutes.

CT IMAGING 100 ml of 8 ml I/ml formulation was administered to a 3.5 kg unfasted rabbit 5 h before CT imaging. The formulation provided a uniform GI opacification, mixed quite well with the GI content and the images obtained were compared with CT results obtained with other conventional agents. The images obtained with conventional agents were much inferior.

The invention having been fully described, it will be apparent to one skilled in the art that changes and modifications can be made thereto without departing from the spirit and scope thereof.

What is claimed is:

1. A method of carrying out x-ray examination of the gastrointestinal tract of a patient, said method comprises the oral or rectal administration to the patient of an aqueous x-ray contrast formulation comprising:

from about 0.001 to about 75% w/v of an x-ray contrast agent having the formula:

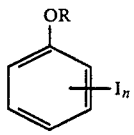

wherein R is a substituted or unsubstituted alkyl group containing from 2 to 8 carbon atoms, wherein said substituent is selected from the group consisting of $C_1$–$C_6$ alkyl, hydroxy and alkoxy; n is 1 to 5;

said x-ray contrast agent being in the form of an aqueous dispersion in said composition wherein said dispersion contains from about 0.01 to about 5% w/v of at least one surfactant selected from the group consisting of cetyl trimethyl ammonium bromide, sodium lauryl sulfate, sodium heptadecyl sulphate, an alkyl benzensulphonic acid, sodium butylnaphthalene sulfonate, sulphosuccinate, a carboxylic ester, a carboxylic amide, an ethoxylated alkylphenol, an ethoxylated aliphatic alcohol, sorbitan ester, a polyoxyethylene alkyl ether, a polyoxyethylene sorbitan fatty acid ester and a zwitterionic surfactant.

2. The method of claim 1 wherein the amount of contrast agent administered to said patient contains from about 0.1 to about 16 g iodine/kg body weight for regular X-ray visualization of the gastrointestinal tract.

3. The method of claim 1 wherein the amount of contrast agent administered to said patient contains from about 1 to about 600 mg iodine/kg body weight for CT scan visualization of the gastrointestinal tract.

4. The method of claim 1 wherein said X-ray contrast agent is in the form of an emulsion.

* * * * *